United States Patent [19]

Vora

[11] 4,073,823
[45] Feb. 14, 1978

[54] ALKYLATION PROCESS UTILIZING HF REGENERATOR STREAM TO A MULTI-TRAY MAIN FRACTIONATOR

[75] Inventor: Bipin V. Vora, Wheeling, Ill.

[73] Assignee: UOP Inc., Des Plaines, Ill.

[21] Appl. No.: 793,225

[22] Filed: May 2, 1977

Related U.S. Application Data

[63] Continuation-in-part of Ser. No. 660,900, Feb. 24, 1976, abandoned, which is a continuation-in-part of Ser. No. 533,421, Dec. 16, 1974, Pat. No. 3,956,416.

[51] Int. Cl.$^2$ .............................................. C07C 3/54
[52] U.S. Cl. .............................................. 260/683.48
[58] Field of Search ............... 260/683.48; 208/351

[56] References Cited

U.S. PATENT DOCUMENTS

| | | | |
|---|---|---|---|
| 3,371,032 | 2/1968 | Witt et al. | 208/351 |
| 3,410,759 | 11/1968 | Fontenot et al. | 260/683.48 |
| 3,478,125 | 11/1969 | Chapman | 260/683.48 |
| 3,763,265 | 10/1973 | Hutson, Jr. et al. | 260/683.48 |
| 3,879,488 | 4/1975 | Anderson et al. | 260/683.48 |
| 3,956,416 | 5/1976 | Vora | 260/683.48 |

Primary Examiner—George Crasanakis
Attorney, Agent, or Firm—James R. Hoatson, Jr.; Richard D. Stone; William H. Page, II

[57] ABSTRACT

A motor fuel HF alkylation system which eliminates the overhead system of the HF acid regenerator is disclosed. The overhead vapors from the regenerator are injected directly into the main fractionator used to separate alkylation reactor effluent into alkylate, isoparaffins and propane.

5 Claims, 1 Drawing Figure

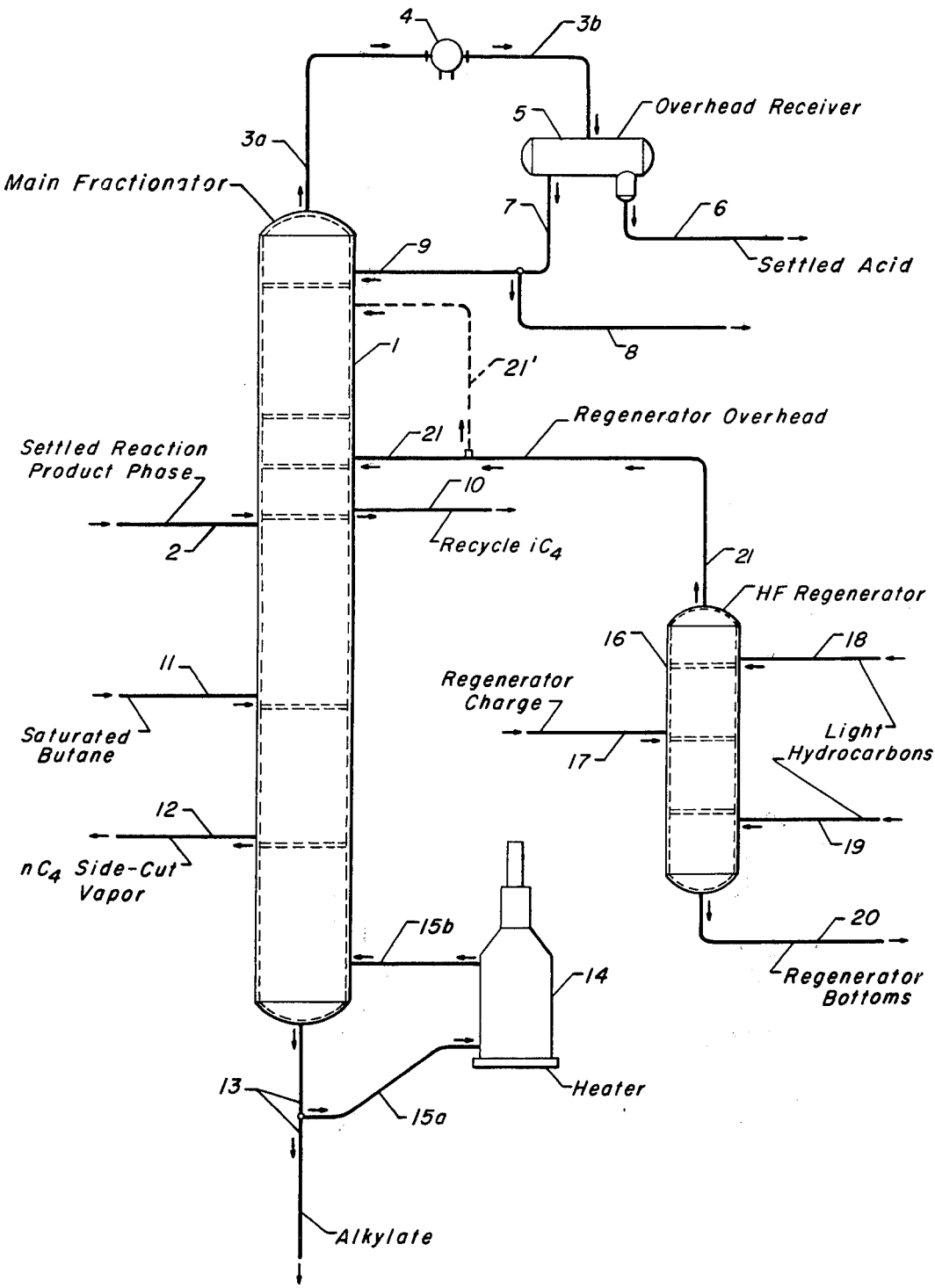

ALKYLATION PROCESS UTILIZING HF REGENERATOR STREAM TO A MULTI-TRAY MAIN FRACTIONATOR

CROSS-REFERENCE TO RELATED APPLICATIONS

This application is a continuation-in-part of my copending application Ser. No. 660,900, filed on 24 Feb., 1976 and now abandoned, which is a continuation-in-part of my application Ser. No. 533,421, filed on 16 Dec. 1974, now U.S. Pat. No. 3,956,416, and the teachings of both applications are incorporated by reference.

BACKGROUND OF THE INVENTION

This invention relates to a catalytic alkylation process. It particularly relates to an improved process for the separation of the hydrocarbon and acid components present in the effluent from a catalytic alkylation zone. It specifically relates to an improvement to eliminate the overhead vapor apparatus of the HF regenerator, including the overhead condenser, overhead receiver, and overhead pump.

It is well known in the prior art that catalytic alkylation using hydrofluoric acid or sulfuric acid as the catalyst has become an important chemical tool for preparing alkylated hydrocarbons and derivatives thereof. The commercial and industrial demand for these products is exemplified with the demand for isoparaffin hydrocarbons and alkyl-substituted benzenes of gasoline boiling range and with the demand for alkyl-substituted aromatics suitable for conversion to surfactants, e.g., detergents, wetting agents, etc. The prior art process of alkylation generally is effected by contacting an isoparaffin hydrocarbon feed stock with an olefin hydrocarbon in the presence of a catalyst such as hydrofluoric acid in a suitable reaction vessel for conducting chemical reactions.

In practice, there have been numerous process schemes advanced by the prior art for accomplishing the alkylation reaction, but it is extremely difficult to achieve a process scheme which embodies all of the desirable features of a completely optimum reaction. Optimizing the alkylation reaction is complicated by the fact that the alkylation reaction if not carried out properly has many side reactions, such as polymerization, which destroys the effectiveness of the reaction and inhibits the production of commercial quantities of desired alkylate. Additionally, the reaction, in order to be carried out commercially, requires a tremendous amount of auxiliary equipment for the recovery of the alkylate product, for the regeneration and reuse of the excess catalyst, and for the recovery and reuse of the excess reactants which have passed through the reaction system.

The catalytic alkylation process to which the present invention is applicable consists of a process in which a mixture of hydrocarbons containing isoparaffins such as isobutane, isopentane, and the like, and olefins such as propylene, butenes, isobutenes, and the like, are mixed intimately in the presence of a strong acid catalyst, such as hydrofluoric acid or sulfuric acid at generally room temperatures or lower for sufficient time to complete the reaction. The effluent from the reaction zone contains saturated isoparaffin hydrocarbons of higher molecular weight or boiling point than the isoparaffin in the original mixture. For convenience, these higher molecular weight isoparaffin hydrocarbons which comprise the reaction product from the alkylation zone are called "alkylate." Isobutane has been used almost exclusively because of its reactivity and availability to produce high quality alkylate product. In similar manner, among the olefins, butenes and propylenes have been used satisfactorily. In some cases it is desirable to use solely propylene or butene as the olefin reactant.

As is typical in most commercial chemical plants, the reaction between the isoparaffin hydrocarbon and the olefin hydrocarbon is performed with an excess of isoparaffin in the reaction zone. Accordingly, there is a large excess of the isoparaffin hydrocarbon remaining in the effluent from the reaction zone. Additionally, there is a significant quantity of $C_3$ hydrocarbons which pass through the system, and for economy sake, must be recovered in as high yield as possible. In similar manner, it is desirable to recover for reuse the isoparaffin reactant in as high yield as possible, which is accomplished in an isoparaffin stripper, or, more specifically when isobutane is the isoparaffin, an isostripper.

In my prior application, U.S. Ser. No. 533,421, now U.S. Pat. No. 3,956,416, I disclosed an HF alkylation process wherein the reactor effluent was separated into a hydrocarbon phase and an acid phase, and the hydrocarbon phase passed through a train of two fractionators. The first fractionator was an isobutane stripper which produced a bottoms fraction of pure alkylate, a n-$C_4$ side-cut vapor fraction, a recycle isobutane side-cut vapor fraction, and an overhead fraction of isobutane and lighter materials. The overhead fraction was charged to a depropanizer, to remove propane from isobutane. The advantage of operating with two fractionators is that the overall pressure of the system is much lower than if this same fractionation were attempted in a single column.

It is also know to operate fractionation columns so that a liquid isobutane recycle stream is obtained. The fractionation scheme disclosed in my copending application mentioned above would be most suitable for obtention of a vapor phase isobutane recycle stream. In U.S. Pat. No. 3,371,032 (Class 208-351), the teachings of which are incorporated by reference, a fractionator is disclosed which will permit recovery from the fractionator of an isobutane-rich stream which is in the liquid phase. A relatively pure propane stream is recovered overhead in such a system. When a single fractionator is used in this fashion, it will be called a "main fractionator." This terminology is in contrast to the two fractionator system of my prior patent, which requires an isobutane stripper and a separate depropanizer.

The process of the present invention should not be confused with that disclosed in U.S. Pat. No. 3,763,265 (Class 260-683.42). In that patent a fractionator is disclosed which provides for the addition of makeup and/or re-run HF acid to the upper portion of a fractionator, with a side-out recycle isobutane stream being withdrawn from a lower portion of the fractionator. This is merely a conventional fractionator combined with an extractive distillation zone. The conventional fractionator operates to produce vapors containing essentially propane and ethylfluoride and a liquid-containing propane and alkylfluoride, and subjecting these vapors and liquids to extractive distillation with hydrogen fluoride. Liquid hydrogen fluoride is introduced to the top of the extractive distillation zone to absorb ethylfluorides so that they can be returned, in solution in HF acid, to the alkylation zone. The process works better with higher purity HF acid, so the patentee provides for the introduction of makeup HF, or re-run HF, or HF which is recovered from the overhead of a conventional depropanizer. Such an operation, wherein extractive distillation is practiced using a liquid HF acid phase to absorb ethylfluorides, and wherein a recycle isobutane stream is withdrawn from a fractionator does not come within the scope of the present invention.

Another problem associated with the operation disclosed in U.S. Pat. No. 3,763,265 is that the fractionation of the liquid HF added to the top of the fractionator is relatively inefficient, while contributing substantially to the heating load of the column.

The fractionation of this liquid HF fraction is inefficient because a lot of the liquid will be vaporized and go overhead immediately after entering the fractionator. Addition of hydrocarbon reflux, via line 30, to a point above the inlet point of the HF acid line 24, will absorb some of the vaporized HF acid added, but there will still be a very large amount of HF acid vapor going overhead in this fractionator. There is a significant loss of entropy of the system in adding a relatively pure HF acid stream via line 24, and then adding above this stream a relatively pure hydrocarbon fraction via line 30. Quite a lot of work was accomplished in obtaining these two streams in a relatively pure state, and quite a lot of work will be lost in mixing them together at that point in the fractionator with no benefit obtained thereby.

The heating load of the column will be increased because the HF acid added via line 24 must either be vaporized and removed from the system via line 9, or must be eventually recovered as a hotter liquid via line 22. The net effect will be to increase the amount of heat which must be added to the bottom of the column.

To recover propane product in the overhead 9 while maintaining a liquid HF phase 22 would require substantial reflux thru line 30 and line 20. HF requires substantially more energy for vaporization compared to the $C_2$–$C_4$ hydrocarbons on the same unit base. More reflux and more heat input to subsequently vaporize this reflux are necessary to maintain this operation.

In contrast, addition of a vapor phase HF hydrocarbon mixture fraction to this column will not increase the heating requirement. As a matter of fact, since these vapors are superheated, and consist of HF and $C_3$ or $iC_4$, the heating requirement will decrease.

If propane is used as a stripping medium in the regenerator, both $C_3$ and HF are overhead vapor products, at a temperature lower than their inlet to the column. Thus it will reduce the heating requirement.

If $iC_4$ is used as the stripping medium the $iC_4$ portion goes with the $iC_4$ side cut (liquid) and HF as overhead vapor. Again for the same fractionation it will reduce the reboiler load.

Addition of an overhead vapor or liquid stream from an HF acid regenerator to this fractionator at some point several trays below the top of the fractionator would also increase the efficiency of the operation. The efficiency would be increased because the overhead fraction from an HF acid regenerator can be very cheaply fractionated in the main fractionator, and fractionation of this stream is very important.

Presuming that e.g., isobutane is used as the stripping medium in the HF acid regenerator, to use the isobutane portion of the regenerator overhead to benefit the alkylation reaction would require a condenser and a phase separator. The liquid isobutane phase then can be recycled to the alkylation reactor to increase the $iC_4$/olefin ratio which will improve the alkylate quality. Even then the benefit is partial, as the liquid $iC_4$ from the phase separator contains dissolved HF which, when it comes in contact with the olefins prior to the reaction chamber, where the acid concentration is substantially low, gives poor reaction products. Thus any contact of HF with olefin outside the alkylation reactor must be avoided or minimized as much as possible.

A discussion of this problem, and another means of solving it is disclosed in U.S. Pat. No. 3,879,488, the teachings of which are incorporated herein by reference. For the present discussion, it is enough to note that for the isobutane stripping agent used in the HF acid regenerator to be reused again in the HF alkylation zone, it must be subjected to fractionation to permit recovery of an isobutane fraction which is not saturated with HF acid.

If propane is used as a stripping medium, introducing the regenerator overhead vapors to the main fractionator just below the reflux (2–5 trays) would reduce the heat load on the column, but all the propane and HF will be recovered as overhead vapor product. This scheme also saves the cost of an acid regenerator separator condenser receiver and transporting system.

Briefly restated, addition of condensed liquid derived form the overhead vapor of a conventional HF acid regenerator will increase the heat requirement of the fractionator receiving this material. Addition of either a vapor or liquid stream from the regenerator to the top of a fractionator will waste energy as this will not be the optimum feed point location.

Accordingly one skilled in the art would be reluctant to use the process disclosed in the U.S. Pat. No. 3,763,265, unless needed to overcome an extraordinary problem, namely the recovery of ethyl fluorides. Ethyl fluorides are not a significant problem in most alkylation processes, and refiners would be reluctant to pay the onerous cost of utilities involved with such a process unless they were encountering significant problems with ethyl fluoride accumulation or loss.

In these catalytic alkylation processes there is a need for periodic regeneration of the catalyst system. This was usually accomplished by taking a stream of at least a portion of the acid catalyst, e.g., hydrofluoric acid, and passing it to a regeneration column wherein the regenerated catalyst is stripped with a light hydrocarbon, for example, hot or superheated vaporous isobutane. The purpose of this regeneration is to remove from the catalyst impurities such as water and acid soluble oils which accumulate in the system. These oils are of a polymeric composition which is in equilibrium with the alkylate hydrocarbon and heavy tar produced in the alkylation reaction. As used in this specification, these impurities and/or contaminants in the catalyst phase are for convenience lumped together and characterized as being material boiling above the boiling point of hydrogen fluoride acid.

The prior art processes for regenerating liquid catalyst such as hydrofluoric acid catalyst usually involve distillation schemes which present problems both from a process standpoint and from an apparatus standpoint. For example, since it is an acid system, the presence of water will cause severe corrosion problems in the regeneration column and in any condensing means associated therewith. Expensive, high quality alloy metallurgy is provided in the various apparatus associated with the regenerator to reduce the rate of corrosion found in this system, and even so, frequency replacement of equipment is not unusual. In addition, sufficient heat must be applied to the catalyst stream in order to vaporize the catalyst for recovery as a purified product. However, in the vaporization of this catalyst stream there will remain a non-vaporized residue of heavy organic diluent which tends to foul the tubes of the heat inducing means. Another problem present in the prior art process is the difficulty of providing sufficient stripping media so that the acid losses to the tar residue are minimized. If sufficient stripping media is passed into the regeneration column so that no acid will remain in the bottom product, there is frequently entrained overhead an excessive portion of heavy organic diluent which then contaminates the vaporized catalyst stream thereby creating additional fouling problems in the lines and condensing means associated with the regeneration system.

In the prior art, several means have been used to eliminate the HF generator overhead system, which can be described as the overhead condenser, overhead receiver, and overhead pump, or to combine that system with the overhead system of another fractionation apparatus. Thus it is seen in U.S. Pat. No. 3,349,146 that the regenerator overhead system is combined with the overhead system of a fractionator which strips HF from propane. Also in the prior art, in an isobutane stripper system wherein isobutane recycle is withdrawn from the isobutane stripper system as condensed overhead vapor saturated with HF, the overhead vapors of the HF regenerator are introduced into the overhead vapor conduit of the isobutane stripper upstream of the overhead condenser, thereby eliminating the regenerator overhead system. However, in the modern isobutane stripper, recycle isobutane is withdrawn as a side-cut from the isobutane stripper, and all overhead hydrocarbon product is withdrawn as feed to subsequent fractionation, i.e., depropanization. When the modern isobutane stripper came into use, it was considered desirable to separate the overhead systems of the regenerator and isobutane stripper in an effort to reduce incremental capital and operating costs of the depropanization fractionation, which wre deemed greater than the incremental capital and operating costs of the separate regenerator overhead system.

Another prior art way of eliminating the overhead system of the HF regenerator is disclosed in U.S. Pat. No. 3,478,125 (Class 260–683.48), the teachings of which are incorporated by reference. In this patent, the overhead fraction, comprising HF acid and stripping vapors is returned to the settler or alternatively to the reaction zone. Such a system will eliminate the overhead system in a regenerator, but is not a complete solution. If the overhead fraction from the HF regenerator is added to the settler, the heat of condensation of this stream may be adsorbed by the acid phase, which is generally undesirable, as it results in a higher temperature in the reaction zone, or it may be adsorbed by the hydrocarbon phase. If the HF vapors are charged into the portion of the settler containing hydrocarbon liquid, there will be a significant increase in the amount of HF acid which enters the fractionator. Further the HF acid, and its accompanying stripping agent, will be condensed in the settler, only to be vaporized in the fractionator. The major point is that the isobutane needed for stripping is circulating through the fractionation zone without any benefit as recycle. These difficulties will not preclude use of such a system, but decrease somewhat the energy efficiency of an HF alkylation unit. It would be desirable if the vaporized HF acid and stripping vapor could be charged to a fractionator operating at conditions similar to those encountered in the HF regenerator. By matching the conditions in the HF regenerator to the fractionation means used to separate acid from stripping vapor, the net increase in entropy of the system is minimized, and hence utility cost are minimized.

SUMMARY OF THE INVENTION

Accordingly, it is an object of the present invention to provide an improvement in the regeneration of spent acid alkylation catalyst and an improvement in the fractionation of alkylation products.

It is a specific object of this invention to provide an improvement for regeneration of HF catalyst in a more economical and facile manner.

Accordingly, the present invention provides a process for producing an alkylation reaction product from an isoparaffin reactant and an olefin-acting reactant using liquid HF catalyst wherein said reactants and said catalyst are admixed in a reactor at alkylation conditions, a reactor effluent is settled to form a settled HF phase containing acid soluble oils and a settled hydrocarbon product phase containing alkylate product and unreacted isoparaffin reactants, said product phase is fractionated in a multi-tray fractionator having an overhead vapor withdrawal locus at the top for removal of HF dissolved in the hydrocarbon product phase, an alkylate product withdrawal locus at the bottom of said fractionator for withdrawal of alkylate product, a feed point at an intermediate locus of said fractionator for addition of said settled hydrocarbon product phase thereto, and an isoparaffin reactant withdrawal locus above the feed point, and wherein at least a portion of said settled HF is introduced to an HF regenerator and therein contacted at regeneration conditions with a light hydrocarbon stripping medium to strip HF from said acid soluble oils, acid soluble oils are withdrawn from a lower part of said regenerator and HF and said stripping medium are withdrawn as a vapor phase from the overhead of said regenerator, cooled and condensed and charged to conventional phase separation means, the improved method which comprises introducing the regenerator overhead vapor without intermediate cooling and condensation thereof, directly to said fractionator, at a locus at least two theoretical trays below the top and above said isoparaffin withdrawal locus and wherein the fractionation conditions in said fractionator are maintained to prevent formation of a separate liquid hydrogen fluoride phase within said fractionator.

The description of the present invention will be limited to the processing scheme for handling the effluent from a conventional isobutane/mixed olefin alkylation reaction zone, although the scope of the invention is not necessarily to be limited thereto. The effluent is prepared by means known to those skilled in the art, and generally, comprises the steps of commingling an olefin-containing feedstock with an isobutane-containing feedstock and passing the mixture into a conventional alkylation reaction zone. An isobutane-rich recycle stream is also added to the reaction zone in order that the isobutane to olefin mol ratio in the presence of the catalyst is maintained at the proper level. Means for removing the heat of reaction from the reaction zone must be provided and the contact time in the reactor is maintained for a period sufficient to intimately mix and contact the feed mixture with the catalyst so that the alkylation reaction can occur. The total effluent from the reaction zone is generally removed and passed into a separation means whereby an acid phase containing acid soluble oils is separated from a hydrocarbon reaction product phase, generally by settling. The acid is returned to the reactor, preferably by gravity flow in admixture with fresh acid, as needed, and the hydrocarbon reaction product phase is further processed as described hereinbelow. A portion of the acid phase is also passed to a regeneration zone by this invention in conjunction with the process of the hydrocarbon phase.

Conventional alkylation conversion conditions of temperature, pressure, isobutane-olefin mol ratio, and hydrogen fluoride-hydrocarbon volume ratio, can be employed advantageously in the reaction zone. For example, the alkylation of isobutane with a feed comprising propylene and butenes can be carried out at temperatures between 0° F. and 140° F., preferably between 80° F. and 110° F., at pressures sufficiently high to keep the hydrocarbons and catalyst in liquid phase, and at isobutane-olefin mol ratios between 2:1 and 20:1, preferably between 10:1 and 15:1. Ratios of isobutane-olefin of at least 2:1 are essential since lower ratios tend to cause polymerization of the olefins with resulting decrease in yield of desirable alkylate product. The volume ratio of catalyst to hydrocarbon charge can be varied considerably. For example, a ratio of 1:1 to 10:1 can be used, preferably at least 2:1 is used. The acid catalyst charged to the reactor can be substantially anhydrous hydrogen fluoride and can have a titratable acidity as low as 65% by weight, but preferably is maintained between 85% and 95% acidity.

As will become more evident from a detailed description of the present invention with reference to the appended drawing, operating in the manner generally described hereinabove and utilizing the improvement of the present invention will produce an alkylate product having an end point below 400° F, and an unleaded Research Octane Number of at least 92 with a hydrogen fluoride catalyst consumption generally of less than 0.2 pounds of catalyst per barrel of alkylate produced. Additionally, significant economy of operation is achieved over the process schemes taught by the prior art.

Hydrocarbons substantially free from a major proportion of hydrogen fluoride catalyst are withdrawn from the settler vessel associated with the alkylation reaction zone, and are introduced as a settled reaction product phase into the main fractionator. The main fractionator separates propane, lower boiling isobutane, higher boiling n-butane, and reactor effluent product, namely, alkylate.

Frequently, a saturated butane stream including isobutane is available within a refinery from another processing unit. The isobutane in such as saturated butane stream is a desirable feed to an alkylation reaction system, however, it is often beneficial to make a separation of the isobutane from n-butane prior to introducing such a stream to the alkylation reaction zone. For this reason, a saturated butane stream may be introduced as a secondary inlet stream to the main fractionator and the n-butane in that stream plus whatever n-butanes present in the settled reaction product phase removed from the alkylation unit as a side-cut vapor product stream containing principally n-butane. The isobutane in the saturated butane stream principally is withdrawn from the main fractionator as a liquid side-cut recycle stream, which is passed to the alkylation reaction zone.

The main fractionator overhead vapors are condensed and cooled to about 60° to 140° F., introduced into an overhead receiver, and separated into a settled acid phase and a settled hydrocarbon overhead phase, saturated with HF. The settled acid phase is withdrawn from the overhead receiver, and passed to the reaction zone. The settled hydrocarbon overhead phase consisting principally of propane is withdrawn from the overhead receiver, an aliquot portion is recycled to the main fractionator as reflux, and a second aliquot portion is taken as an overhead product stream.

Recycle isobutane is withdrawn at a suitable locus of the main fractionator preferably above the feed tray, A liquid, rather than a vapor stream, is withdrawn. The side-cut recycle stream, when cooled to alkylation reaction temperatures will contain less than saturation quantity of HF and about 60 to 95 weight percent isobutane. When compared with recycle isobutane withdrawn as an overhead stream from an isobutane stripper, recycle isobutane withdrawn as a side-cut stream will contain less HF and less propane, which is considered beneficial to higher alkylate quality and lower capital and operating costs.

In alternative embodiments, the main fractionator may be fragmented into three fractionators, wherein an overhead fraction comprising propane and some isobutane is sent to an HF stripper, and the bottoms comprising alkylate and some n-$C_4$ is charged to a separate bottoms fractionator to separate n-$C_4$ and alkylate.

Regardless of the type of product fractionator used, all will have in common the feature of introduction of HF acid regenerator overhead vapors into some locus of the fractionator, which will vary somewhat with the type of stripping vapor used. In general, the use of a propane stripping vapor will indicate that the optimum point in the main fractionator for adding regenerator overhead vapors will be fairly high up in the column, to match the composition of the regenerator overhead vapors with the composition of the material in the main fractionator of that point. Preferably, the stripping agent used in the HF regenerator is an isobutane fraction, in which case the point of introduction of regenerator overhead vapors into the main column will be close to but slightly above the point of withdrawal of recycle isobutane. It is preferred to add the HF regenerator overhead vapor above the recycle isobutane stream withdrawal point to minimize contamination of recycle isobutane with HF.

I have found that when propane is the stripping agent, at least two theoretical stages of separation should be maintained between the point of injection of the HF acid regnerator overhead vapors and the top of the fractionating column. A feed point any higher than this location would result in significant loss the energy associated with these vapors. Adding the vapors to the very top of the fractionator would mean that essentially no heat transfer would occur as both HF and $C_3$ are recovered as overhead product. Providing at least two theoretical stages and preferably five of fractionation permits proper heat exchange, the regenerator overhead vapors provide vapor traffic necessary at the top, which otherwise must be provided by the reboiler or other heat source.

When isobutane stripping agent is used in the HF acid regenerator, a significantly lower feed point is desired. It is desirable that the feed point be above the $iC_4$ draw off. A preferable location would be 2–4 trays above the $iC_4$ draw off so that HF stripping can be accomplished and $iC_4$ can be recovered with the $iC_4$ draw off. Adding the overhead vapors higher up in the column would result in significant contamination of the isobutane stripping agent with propane which concentration would be higher in the upper portion of the column. Thus the situation using $iC_4$ stripping agent is significantly different than that when using $C_3$ stripping agent, as no separation of $C_3$-HF is desired, both are overhead products.

In my prior application, I stated, erroneously, that if a pure propane stripping agent was used then it should enter the main fractionator at the top tray, see the bottom of Table II of my prior application. The vast majority of HF acid regenerators use isobutane as a stripping agent. However, use of pure propane stripping agent is feasible and would increase, or elevate, the optimum feed point location of this stream, but would not make addition to the top tray the ideal location. As previously mentioned, addition of a vapor stream to the top tray of the fractionator would result in loss of potential energy benefits which may be recoverable from the regenerator overhead vapors.

The HF regenerator design is familiar to one skilled in the art. A portion of the HF acid containing acid soluble oils is withdrawn from the reactor/settler system and introduced directly or heated to about 150° to 300° F. and introduced into the regenerator at about the middle tray. A cooled light hydrocarbon liquid stream at about 80° to 150° F. is introduced as reflux above the top tray of the regenerator and a superheated light hydrocarbon vapor stream at about 300° to 500° F. is introduced below the bottom tray. The cooled light hydrocarbon liquid stream and superheated light hydrocarbon vapor stream, preferably principally isobutane, are withdrawn from the bottom section of the depropanizer as liquid and vapor streams, respectively. The trays of the regenerator may be sieve type or valve type. Liquid acid soluble oils are withdrawn from the regenerator bottom at a temperature of about 350° F. and a regenerator overhead vapor stream of HF and hydrocarbon containing mostly isobutane is withdrawn from the top at about 150° to 200° F. and a pressure of about 100 to 350 psig. The disposition of the regenerator overhead vapor stream is the subject of the present invention. In the prior art, said regenerator overhead vapor stream is combined with the overhead stream of a fractionator stripping HF from propane or the overhead stream of an isobutane stripper, or condensed, cooled, and passed to the alkylation reaction zone, etc. In the present invention, the regenerator overhead vapor stream is introduced into the isobutane stripper or main fractionator at a locus above the locus at which the sidecut isobutane recycle stream is withdrawn. The HF in the regenerator overhead vapor stream is principally withdrawn from the isobutane stripper or main fractionator as part of the overhead vapor stream, condensed, and passed to the reaction zone as HF liquid, while the hydrocarbon in the regenerator overhead vapor stream is withdrawn from the isobutane stripper principally in the side-cut recycle isobutane stream. As compared to introducing a regenerator overhead vapor stream into an isobutane stripper overhead vapor stream, the practice of the present invention will reduce the isobutane concentration of the isobutane stripper settled hydrocarbon overhead phase and result in lower capital and operating costs of the isobutane stripper-depropanizer fractionation systems, at the same time maintaining HF in the side-cut isobutane recycle stream below the saturation point of HF when the recycle stream is cooled to alkylation reaction temperature. The isobutane separation described above is accomplished by the fractionation which occurs between the top of the isobutane stripper and the locus at which the regenerator overhead vapor stream is introduced into the isobutane stripper, resulting in a substantial portion of the isobutane in that stream passing into the side-cut recycle isobutane stream while a relatively small portion passes into the isobutane stripper overhead vapor stream and subsequently into the overhead product stream.

When a single large fractionator, or main fractionator, is used instead of an isostripper, then propane may be used as the stripping agent. In this case the regenerator overhead vapors will enter the main fractionator fairly high up in the fractionator.

DESCRIPTION OF THE DRAWING

An understanding of this invention may be aided by reference to the accompanying drawing which represents a schematic flow diagram of an embodiment of the invention. Many variations and modifications within the scope of this invention will be obvious to one skilled in the art from the description herein provided. Alkylation reaction zone effluent is separated to form a hydrocarbon settled reaction product phase stream which is introduced as a feed into main fractionator 1 via conduit 2. An overhead vapor stream is withdrawn via conduit 3a, condensed and cooled in exchanger 4 and introduced via conduit 3b into overhead receiver 5. A settled acid phase and a settled hydrocarbon overhead phase are separated in overhead receiver 5. The settled acid phase is withdrawn via conduit 6 and passed to the reaction zone. The settled hydrocarbon overhead phase is withdrawn via conduit 7, a first portion passing via conduit 8, as a product stream and for use as stripping medium, and a second portion passing to the top of the main fractionator as reflux via conduit 9. At a tray above the feed tray, a liquid side-cut recycle stream containing principally isobutane is withdrawn via conduit 10. A saturated butane stream may be introduced into main fractionator 1 via conduit 11. A principally n-butane side-cut vapor stream is withdrawn via conduit 12, and an alkylate product stream is withdrawn from the bottom via conduit 13. Heat is supplied to the main fractionator by heater 14 in bottoms conduits 15a and 15b.

Simultaneous with the operation of the main fractionator described hereinabove, a portion of HF acid containing acid soluble oils is withdrawn from a settled catalyst phase of the alkylation reaction zone effluent and introduced into regenerator 16 via conduit 17. A light hydrocarbon stream rich in propane and originating in the main fractionator is introduced as a reflux liquid to the top of regenerator 17 via conduit 18, and a second light hydrocarbon stream of similar source and content is introduced as a stripping vapor below the bottom tray of the regenerator via conduit 19. Acid soluble oils are withdrawn via conduit 20 from the regenerator bottom. From the top of the regenerator, a regenerator overhead vapor stream containing stripped hydrogen fluoride and light hydrocarbon are withdrawn via conduit 21 and introduced into main fractionator 1 well above the feed tray and the tray at which the side-cut recycle stream is withdrawn.

EXAMPLE

Shown herein below is a mole balance by component of the inlet and outlet streams of a main fractionator and an HF regenerator, for two cases with constant alkylation reaction conditions: (I) separate HF regenerator and main fractionator overhead vapor systems; (II) HF regenerator overhead vapor stream flows into the main fractionator at a locus above the feed stream inlet and above the isobutane recycle stream outlet.

The main fractionator operating conditions are:

Pressure = 300 psig
Bottoms Temp. = 450° F
Top Temp. = 140° F
Liquid Recycle (line 10) = 220° F The regenerator operating conditions are:

Pressure = 310 psig
Bottoms Temp. = 370° F
Overhead Temp. = 220° F
Stripping Vapors (line 19) = 450° F

TABLE I

| | Separate Regenerator and Main Fractionator | | | | | | | | | | |
|---|---|---|---|---|---|---|---|---|---|---|---|
| | Main Frac. Feed | n-Butane Product | Alkylate Product | Net Overhead to Phase Separator | Phase Sepa. HC to HF Stripper | Phase Sepa. Acid to Reactor | Liquid Recycle | HF Regen. Charge | Light HC to HF Regen. | Overhead to Condenser (not shown) | Regen. Bottoms |
| Line No. | 2 | 12 | 13 | 3a | 8 | 6 | 10 | 17 | 18 + 19 | 21 | 20 |
| HF | 357 | — | — | 340.15 | 5.85 | 334.30 | 16.85 | 323 | — | 322 | 1 |
| $C_2$ | 6 | — | — | 4.57 | 4.57 | — | 1.43 | — | — | — | — |
| $C_3$ | 1,268 | — | — | 260.12 | 260.12 | — | 1,007.88 | — | 43 | 43 | — |
| $iC_4$ | 10,093 | 118.49 | 24.80 | 0.16 | 0.16 | — | 9,949.55 | — | 421 | 421 | — |
| $nC_4$ | 1,174 | 190.11 | 65.97 | — | — | — | 917.92 | — | 39 | 39 | — |
| $iC_5$ | 404 | 84.80 | 182.12 | — | — | — | 137.08 | — | 8 | 8 | — |
| $nC_5$ | 62 | 11.46 | 33.74 | — | — | — | 16.80 | — | — | — | — |
| $C_6+$ | 908 | 21.14 | 854.37 | — | — | — | 32.49 | — | — | — | — |
| Other | — | — | — | — | — | — | — | 5 | — | — | 5 |
| TOTAL | 14,272 | 426.00 | 1,161.00 | 605.00 | 270.70 | 334.30 | 12,080.00 | 328 | 511 | 833 | 6 |

(In this case regenerator overhead must be condensed to separate HF phase and hydrocarbon phase. The hydrocarbon phase is reheated and reused for stripping. The acid phase is returned to the reactor. Both phases require separate pumping systems.)

TABLE II

Regenerator Overhead to Main Fractionator
(those streams with changed compositions shown)

| | Regen. Overhead to Main Frac. | Net Overhead to Phase Separator | Liquid Recycle |
|---|---|---|---|
| Line No. | 21 | 3a | 10 |
| HF | 322 | 662.15 | 16.85 |
| $C_2$ | — | 4.57 | 1.43 |
| $C_3$ | 43 | 260.12 | 1,050.88 |
| $iC_4$ | 421 | 0.16 | 10,370.55 |
| $nC_4$ | 39 | — | 956.92 |
| $iC_5$ | 8 | — | 145.08 |
| $nC_5$ | — | — | 16.80 |
| $C_6+$ | — | — | 32.49 |
| Other | — | — | — |
| TOTAL | 833 | 927.00 | 12,591.00 |

(Regenerator overhead is charged into the main fractionator. Feed location of regenerator overhead to isostripper should be above liquid recycle cut. Preferably 3-4 trays above with the above composition.
If the hydrocarbon to the acid regenerator were richer in propane, this feed location move upward.

I claim as my invention:

1. In a process for producing an alkylation reaction product from an isoparaffin reactant and an olefinacting reactant using liquid HF catalyst wherein said reactants and said catalyst are admixed in a reactor at alkylation conditions, a reactor effluent is settled to form a settled HF phase containing acid soluble oils and a settled hydrocarbon product phase containing alkylate product and unreacted isoparaffin reactant, said product phase is fractionated in a multi-tray fractionator having an overhead vapor withdrawal locus for separation of HF phase and propane product phase, an alkylate product withdrawal locus at the bottom of said fractionator for withdrawal of alkylate product, a feed point at an intermediate locus of said fractionator for introduction of said settled hydrocarbon product phase into said fractionator, and an isoparaffin reactant recycle locus above said feed point, and wherein at least a portion of said settled HF phase is introduced to an HF regenerator and therein contacted at stripping conditions with a light hydrocarbon to strip HF from said acid soluble oils, withdrawing said acid soluble oils from a lower part of said regenerator, the improvement which comprises introducing the regenerator overhead vapor to said fractionator at a locus at least two theoretical trays below the top of said fractionator and above said isoparaffin recycle locus and wherein the fractionation conditions in said fractionator are maintained to prevent formation of a separate liquid hydrogen fluoride phase within said fractionator.

2. The improved process of claim 1 wherein the isoparaffin reactant is isobutane, the olefin-acting reactant is a mono-olefin having from 3 to 5 carbon atoms per molecule and the side cut recycle stream comprises isobutane.

3. The improved process of claim 2 wherein the isoparaffin is withdrawn from said fractionator as a liquid.

4. The improved process of claim 1 wherein the stripping hydrocarbon comprises propane and the regenerator overhead vapor stream is added to said fractionator at a locus two to five theoretical trays below the top of said fractionator.

5. The improved process of claim 1 wherein the stripping hydrocarbon comprises isobutane and the regenerator overhead vapor stream is added to said fractionator at a locus two to five trays above the isoparaffin withdrawal tray.

* * * * *